US007438896B2

(12) United States Patent
Perricone

(10) Patent No.: US 7,438,896 B2
(45) Date of Patent: Oct. 21, 2008

(54) METHOD OF SKIN CARE USING LIPOIC AND ASCORBIC ACIDS

(75) Inventor: Nicholas V. Perricone, Meriden, CT (US)

(73) Assignee: N.V. Perricone LLC, Meriden, CT (US)

( * ) Notice: Subject to any disclaimer, the term of this patent is extended or adjusted under 35 U.S.C. 154(b) by 485 days.

(21) Appl. No.: 10/872,938

(22) Filed: Jun. 21, 2004

(65) Prior Publication Data

US 2005/0013783 A1    Jan. 20, 2005

Related U.S. Application Data

(63) Continuation-in-part of application No. 09/961,766, filed on Sep. 24, 2001, now Pat. No. 6,752,999, which is a continuation-in-part of application No. 09/272,505, filed on Mar. 19, 1999, now abandoned, which is a continuation-in-part of application No. 08/988,117, filed on Dec. 10, 1997, now abandoned, which is a continuation of application No. 08/531,290, filed on Sep. 20, 1995, now Pat. No. 5,709,868.

(51) Int. Cl.
*A61K 31/34* (2006.01)
*A61K 31/355* (2006.01)
*A61Q 19/04* (2006.01)

(52) U.S. Cl. .......................... 424/59; 514/458; 514/474

(58) Field of Classification Search ................. 424/401, 424/59; 514/97, 474, 458
See application file for complete search history.

(56) References Cited

U.S. PATENT DOCUMENTS

| 5,084,481 | A | 1/1992 | Ulrich et al. | 514/557 |
| 5,409,693 | A | 4/1995 | Perricone | 424/59 |
| 5,472,698 | A | 12/1995 | Rawlings et al. | 424/401 |
| 5,569,670 | A | 10/1996 | Weischer et al. | 514/440 |
| 5,574,063 | A | 11/1996 | Perricone | 514/474 |
| 5,646,190 | A | 7/1997 | Martin | 514/724 |
| 5,665,364 | A | 9/1997 | McAtee et al. | 424/401 |
| 5,693,664 | A | 12/1997 | Wessel et al. | 514/440 |
| 5,709,868 | A | 1/1998 | Perricone | 424/401 |
| 5,728,735 | A | 3/1998 | Ulrich et al. | 514/560 |
| 5,972,993 | A | 10/1999 | Ptchelintsev | 514/449 |
| 6,296,861 | B1 | 10/2001 | Perricone | 424/401 |
| 6,752,999 | B2 | 6/2004 | Perricone | 424/401 |

OTHER PUBLICATIONS

Lester Packer, Eric H. Witt and Hans Jürgen Tritschler, Alpha-Lipoic Acid As A Biological Antioxidant, Dec. 20, 1994, pp. 227-250.
Nobuya Haramaki, Derick Han, Garry J. Handelman, Hans J. Tritschler and Lester Packer, Cytosolic And Mitochondrial Systems for NADH and NADPH-Dependent Reduction of a Lipoic Acid, Jul. 11, 1996, pp. 535-542.
Free Radical Biology & Medicine, The Official Journal of The Oxygen Society, vol. 25, Supplement 1, 1998.

*Primary Examiner*—Johann Richter
*Assistant Examiner*—Konata M. George
(74) *Attorney, Agent, or Firm*—St. Onge Steward Johnston & Reens LLC

(57) ABSTRACT

Methods for the prevention of skin damage arising from exposure to ultraviolet or solar radiation, using lipoic acid and asorbic acid and/or ascorbic acid derivative in a dermatologically acceptable carrier that can be topically applied to the skin areas. Tocotrienol and/or an α-hydroxy acid such as glycolic acid is applied with the lipoic acid and ascorbic acid an/or its derivatives in some embodiments.

15 Claims, No Drawings

METHOD OF SKIN CARE USING LIPOIC AND ASCORBIC ACIDS

RELATED APPLICATIONS

This is a continuation-in-part of U.S. application Ser. No. 09/961,766 filed Sep. 24, 2001 (to issue as U.S. Pat. No. 6,752,999 on Jun. 22, 2004) which is a continuation-in-part of U.S. application Ser. No. 09/272,505, filed Mar. 19, 1999, now abandoned which is a continuation-in-part of U.S. application Ser. No. 08/988,117, filed Dec. 10, 1997, now abandoned, which was a continuation application of U.S. application Ser. No. 08/531,290, filed Sep. 20, 1995, which issued as U.S. Pat. No. 5,709,868 on Jan. 20, 1998.

FIELD OF THE INVENTION

This invention relates to the topical application of compositions containing lipoic acid and ascorbic acid and/or ascorbic acid derivatives for the prevention and/or treatment of damage to skin.

BACKGROUND OF THE INVENTION

Lipoic acid was originally identified as a bacterial growth factor present in the water-soluble fraction of liver and yeast. It was found to be necessary for the oxidative decarboxylation of pyruvic acid by *Streptococcus fecalis* and for the growth of *Tetrahymena gelii*, and replaced acetate for the growth of *Lactobacillus casei*. It has been variously known as acetate replacing factor, protogen A, and pyruvate oxidation factor.

Subsequent research showed that lipoic acid (LA) was a growth factor for many bacteria and protozoa, and it served as a prosthetic group, coenzyme, or substrate in plants, microorganisms, and animal tissues. Elucidation of its structure and function determined that it is a co-factor for α-keto-dehydrogenase complexes, typically bound as lipoamide, that participates in acyl transfer reactions. Its reduced form, dihydrolipoic acid (DHLA), is a potent sulfhydryl reductant. In aqueous systems, both LA and DHLA exhibit antioxidant actions (reviewed by Packer, L., et al., *Free Rad. Biol. Med.* 19: 227-250 (1995); this and subsequent references are expressly incorporated herein by reference). LA has been shown to maintain microsomal protein thiols, protect against hemolysis, and protect against neurological disorders. The protective effect of dietary supplementation of LA against ischemia/reperfusion injury in the Langendorff isolated heart model has also been demonstrated. LA has been suggested for treating systemically, or as adjuvant systemic medication for, liver cirrhosis, atherosclerosis, diabetes, neurodegenerative diseases, heavy metal poisoning, and Chagas disease (ibid.). It has also been used as an antidote to poisonous mushrooms (ibid., particularly Amanita species, *Merck Index,* 11th ed., 1989, entry 9255).

Few references suggest the use of lipoic acid in dermatological compositions. In a 1988 Japanese patent publication (JP 63008315), lipoic acid in cosmetics at concentrations of 0.01% to 1%, preferably 0.05% to 0.5%, or in topical "quasi-drugs" at concentrations of 0.1% to 1.5%, preferably 0.5% to 1.0%, were suggested for inhibiting tyrosinase, and thus melanin formation, to whiten skin.

In 1992, Ulrich, et al., suggested dihydrolipoic acid or its pharmaceutically acceptable salts, but not lipoic acid (column 3, lines 28 to 29), as having analgesic, anti-inflammatory, and cytoprotective effects (U.S. Pat. No. 5,084,481, column 1, lines 26 to 31) for a number of pathological conditions including inflammatory and non-inflammatory disorders of the skin (column 3, lines 3 to 4).

In 1995, Rawlings, et al., disclosed a composition and method for "improving or preventing the appearance of dry, flaky wrinkled, aged, photodamaged skin and treating skin disorders" (U.S. Pat. No. 5,472,698, column 2, lines 51 to 54) using a synergistic combination of serine and/or N-acetyl serine and a thiol, an "S-ester", and/or a disulfide (id., lines 28 to 33). Lipoic acid was mentioned as encompassed by the latter ingredient (column 3, lines 29 to 30). However, the patent's terminology was confusing. Thiols and S-esters were disclosed as preferable over disulfides (column 4, lines 1 to 4). Though lipoic acid is a disulfide (as shown in the structure below), it's listed as a thiol in the patent (column 3, lines 29 to 30); perhaps what is referred to as "lipoic acid" is, instead, dihydrolipoic acid. This supposition is reinforced by the fact that a Sigma product was employed in some examples (column 7, line 63). Both oxidized lipoic acid and reduced, i.e., dihydrolipoic acid, are available from that chemical company, so DHLA may have been used. Unfortunately, there is more uncertainty about the effects of DHLA when compared to LA (see Packer, et al., cited above, 231-234). The only illustrations of alternate sulfur-containing ingredients were acylated cysteine derivatives, including glutathione.

More importantly, the focus of the patent was stimulation of sphingolipid synthesis in skin to improve it (see column 1 at lines 21 to 23 and column 2 at lines 12 to 13). The examples reported that assays monitored ceramide production in cultured human keratinocytes and porcine skin. In the studies, lipoic acid had no effect in compositions without serine. On the contrary, in every reported assay, the lipoic acid values were identical to controls; see Tables 2 and 3. And, though increasing concentrations of lipoic in the presence of a constant amount of serine boosted ceramide production at certain levels of serine (Table 7), other thiols worked equally well (Tables 1, 4, 5, 6, 8, and 9). Read as a whole, the reference teaches away from LA as an active ingredient, and suggests DHLA of efficacy only with serine or N-acetyl serine.

A year later, in U.S. Pat. No. 5,569,670 to Weischer, et al., pharmaceutical compositions containing a synergistic combination of α-lipoic acid and/or dihydrolipoic acid with specific enantiomers of these, together with some vitamins, including C and E (column 1, lines 3 to 15), were disclosed as useful, primarily for treating diabetes (see the claims). However, anti-inflammatories (abstract, line 8 and column 2 at line 16) as well as treatments for retroviruses and other pathological conditions were included, with an emphasis on veterinary applications (column 13, lines 42 to 62). In a test model for inflammation (observing rat edema), the R-enantiomer of lipoic acid was superior to lipoic alone or to vitamin E alone (column 3, lines 37 to 40). Suggested administration was oral, parenteral or intravenous (column 7, line 31 to end, et seq.), preferably oral (column 11, line 42), but application to skin and mucous membranes was mentioned (column 12, lines 58 to 60). Antioxidants could be employed in some embodiments (column 16, lines 47 to 55), and the list included ascorbic acid, ascorbyl "palmirate" [sic] and tocopherols. The examples combined lipoic and/or dihydrolipoic acid with tocopherols (Examples 1, 2, 5, and 6) or ascorbic acid (Examples 3, 4, and 7). An ointment was disclosed in Example 6; the others described suppositories, capsules, ampules, and tablets.

Similarly, U.S. Pat. No. 5,693,664 to Wessel, et al., from the same research group, was directed to diabetes treatments, particularly where insulin resistance is observed (column 1, lines 10 to 14 and the claims) by use of the R-enantiomer of α-lipoic acid. Again, one enantiomer, not a racemate, was employed (column 6, lines 18 to 19). Indeed, the S-enantiomer decreased the effect of insulin in an experimental study reported (column 3, lines 61 to 65). Suggested administration was primarily oral (column 6, lines 61 to 66), though parenteral and intravenous are mentioned (ibid., and column 3, lines 7 to 8).

U.S. Pat. No. 5,728,735 to Ulrich, et al., again from the same group, stressed use of an enantiomer (column 1, lines 28 to 54), particularly the R-enantiomer (see the claims), and not a racemate, for combatting pain and inflammation in a variety of conditions (id., lines 58 to 59; inflammations are listed in column 5, line 64 to column 6, lines 9 and include neurodermatitis and psoriasis). Suggested administrations were oral, intravenous, or infusions (column 3, lines 28 to 30, 51, 62 to 63 and 65), but solutions and emulsions for topical application were mentioned (column 6, lines 29 to 34 and 65 to 68, and column 8, lines 16 to 18). Only tablets and ampules were illustrated. All the reported findings of the group are complicated by the fact that the metabolic effects of the R- and S-enantiomers are now known to be different, as are the enzymes that process the enantiomers in cytosolic and mitrochondrial systems (Haramaki, N., et al., *Free Rad. Biol. Med.* 22: 535-542 (1997)). Moreover, different stereospecific reduction by intact cells and tissues has also been observed (ibid.).

The antioxidant activity of lipoic acid appears to prevent free radical damage to cells and cell components. Free radical damage is most evident in cellular membranes because of the density of the molecular structure of the membranes. It is currently hypothesized that cell membrane aging leads to all of the various cellular changes seen in aging, such as decreased RNA production, decreased protein production, and faulty enzyme action.

Inflammation in skin is mediated by several active chemicals and metabolites of arachidonic acid. Arachidonic acid is oxidized by cyclo-oxygenase and lipoxygenase to active metabolites such as the leukotrienes and 5- and 12-hydroxyeicosatetraenoic acid (HETES). Within the arachidonic acid cascade, many free radicals are generated, which both perpetuate and magnify the inflammatory cascade, resulting in skin damage and manifested clinically as erythema. Erythema is an abnormal redness of the skin due to dialation of the superficial capillaries of the skin. The redox state of the cell determines gene expression. Transcription factor nuclear factor kappa-B (NFκ-B) is inactive in the cytosol under a normal redox state of the cell. When the cell undergoes oxidative stress, i.e., ultraviolet radiation or ionizing radiation, creating free radicals, the inhibitory fraction of NFκ-B is dissociated from the molecule. Once the inhibitory fraction is dissociated from the NFκB molecule, it then migrates to the nucleus of the cell, begins transcription, and subsequent production of inflammatory mediators, including cytokines such as tumor necrosis factor alpha (TFα) and various interleukins, as well as many of the pro-inflammatory interleukins. These pro-inflammatory and inflammatory products of transcription then enter the cell cytoplasm effecting all parts of the cell including the mitochondria and cell membrane. Arachidonic acid is released, which is oxidized to biologically active mediators. When arachidonic acid is oxidized via the cyclooxygenase or lipoxygenase pathways, for example, prostaglandins, leukotrines, and hydroxyeicosatetraenoic acid (HETE) are produced, which cause erythema, edema, and free radical production. Lipoic acid is a powerful inhibitor of the activation of NFκ-B, and therefore can act to prevent such effects.

Ultraviolet radiation and/or ionizing radiation will cause free radical damage within the cell membrane. The cell membrane is most susceptible to attack by free radicals because of its dense molecular structure largely comprising lipids and lipoproteins, which are easily oxidized by reactive oxygen species. In the epidermis, reactive oxygen species such as singlet oxygen, the superoxide anion, and hydroxyl radicals, as well as other free radicals, are generated through ultraviolet sun exposure and other forms of radiation. These free radicals activate chemical mediators that produce prostaglandins and leukotrines causing erythema.

Early suggestions for dealing with erythema in skin caused by solar exposure (sunburn) were predominantly aimed at lubrications and emollients through use of topical compositions containing soothing agents. More recently, attention has been directed to agents which prevent and treat sunburn by addressing underlying processes involved in skin damage, such as the free radical generation processes. In this regard, investigations have been made with respect to the use of Vitamin C as an antioxidant in sunburn prevention products, as well as in sunburn treatment products. (Wilson, R., *Drug and Cosmetic Industry,* 32-34, 38, and 68, August 1992).

SUMMARY OF THE INVENTION

It is an objective of this invention to provide a method and composition for a preventive regimen and/or therapy based upon topical application to exposed or affected skin areas of at least one active agent, in association with a dermatologically acceptable carrier or vehicle.

These and other objectives are accomplished by the present invention, which provides methods and compositions for the prevention and/or treatment of ultraviolet radiation-induced skin damage, by topically applying to the exposed or affected skin areas of an effective amount of lipoic acid and ascorbic acid and/or ascorbic acid derivatives preferably in a dermatologically acceptable carrier.

Many embodiments incorporate other active ingredients with lipoic acid and ascorbic acid and/or ascorbic acid derivatives. These include tocotrienols or derivatives thereof or vitamin E compositions enriched with tocotrienols or tocotrienol derivatives; and reductants such as α-hydroxy acids, e.g., glycolic acid which augment the efficacy of lipoic acid compositions.

In the preferred practice of the invention, racemic lipoic acid and ascorbic acid and/or ascorbic acid derivatives is applied in admixture with a dermatologically acceptable carrier or vehicle (e.g., as a lotion, cream, ointment, soap, or the like) so as to facilitate topical application and, in some cases, provide additional therapeutic effects as might be brought about, e.g., by moisturizing of the affected skin areas. As noted, other ingredients, particularly tocotrienol and/or glycolic acid are advantageously included in the compositions.

The amount of lipoic acid and ascorbic acid and/or ascorbic acid derivatives necessary to bring about enhanced prevention and/or therapeutic treatment of damage is not fixed per se, and necessarily is dependent upon the identity and form of lipoic acid and ascorbic acid and/or ascorbic acid derivatives employed, the amount and type of any additional ingredients used, particularly those that appear to exhibit synergistic effects (to be discussed more fully below), the user's skin type, and, where present, the severity and extent of the patient's skin damage. Generally, the lipoic acid and ascorbic acid and/or ascorbic acid derivatives or composition containing it is topically applied in effective amounts to skin areas which are susceptible to damage, because of solar exposure.

In one embodiment, the composition contains from about 0.1% to about 5% by weight, preferably from more than 0.5% or 1.5% to about 3%, racemic mixtures of lipoic acid.

In one embodiment, the composition contains from about 0.1% to about 5% by weight, preferably from more than 0.5% or 1.5% to about 3%, ascorbic acid and/or ascorbic acid derivatives.

DETAILED DESCRIPTION OF THE INVENTION

This invention is based upon the finding that a composition of lipoic acid and ascorbic acid and/or ascorbic acid derivatives is useful for the prevention of skin damage arising from exposure to solar radiation. Lipoic acid and ascorbic acid and/or ascorbic acid derivatives compositions also augment the efficacy of other ingredients in topical compositions for sunburn prevention and treatment.

As used herein, the term "lipoic acid" encompasses thioctic acid (1,2-dithiolane-3-pentanoic acid; 1,2-dithiolane-3-valeric acid), $C_8H_{14}O_2S_2$, formula weight 206.32. Lipoic acid was originally identified as a bacterial growth factor present in the water-soluble fraction of liver and yeast. It was found to be necessary for the oxidative decarboxylation of pyruvic acid by *Streptococcus fecalis* and for the growth of *Tetrahymena gelii*, and replaced acetate for the growth of *Lactobacillus casei*. It has been variously known as acetate replacing factor, protogen A, and pyruvate oxidation factor.

Racemic mixtures of lipoic acid, i.e., so-called DL-lipoic or thioctic acid, are preferred in most embodiments, because these are commercially available relatively inexpensively from several chemical and pharmaceutical supply companies. Other embodiments employ the naturally occurring D form and/or its derivatives.

As mentioned above, lipoic acid itself is fat-soluble. Therefore, lipoic acid preparations can be applied neat to skin areas subject to damage or already damaged. It is an advantage of the invention that the active compound is fatty so that it physically contributes to the lubrication and soothing of affected skin areas. Use of fatty acid esters of lipoic acid can contribute to this effect. It is also an advantage of the invention that lipoic acid rapidly penetrates the skin, and freely partitions in the lipid and aqueous portions of cellular components (Packer, et al., cited above).

However, only effective amounts of lipoic acid are needed to prevent skin sunburn damage, so generally topical application to exposed or affected skin sites is accomplished in association with a carrier, and particularly one in which the active ingredient is soluble per se or is effectively solubilized (e.g., as an emulsion or microemulsion). It is necessary that the carrier be inert in the sense of not bringing about a deactivation of the lipoic acid, and in the sense of not bringing about any adverse effect on the skin areas to which it is applied.

Suitable carriers include water, alcohols, oils and the like, chosen for their ability to dissolve or disperse the active ingredients at concentrations of active ingredients most suitable for use in the therapeutic treatment. Generally, even low concentrations of active ingredients in a carrier will be suitable, even as low as 0.1% by weight. As a practical matter, however, to avoid the need for repeated application, it is desirable that the topically applied composition be formulated to contain at least about 0.25% to about 5% by weight, more preferably from about 1% to about 3% by weight lipoic acid, and accordingly, carriers will be chosen which can solubilize or disperse the active ingredients at such concentrations. Many preferred embodiments contain over 1%, and many over 1.5% by weight lipoic acid.

While the carrier for lipoic acid can consist of a relatively simple solvent or dispersant such as oils, it is generally preferred that the carrier comprise a composition more conducive to topical application, and particularly one which will form a film or layer on the skin to which it is applied so as to localize the application and provide some resistance to perspiration and/or one which aids in percutaneous delivery and penetration of the active ingredients into lipid layers. Many such compositions are known in the art, and can take the form of lotions, creams, gels or even solid compositions (e.g., stick-form preparations). Typical compositions include lotions containing water and/or alcohols and emollients such as hydrocarbon oils and waxes, silicone oils, hyaluronic acid, vegetable, animal or marine fats or oils, glyceride derivatives, fatty acids or fatty acid esters or alcohols or alcohol ethers, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophillic colloids. Such compositions are referred to herein as dermatologically acceptable carriers. Most preferred for skin are those carriers which are fat-soluble, i.e., those which can effectively penetrate skin layers and deliver the active lipoic acid to the lipid-rich layers of the skin.

Ascorbic acid (vitamin C) and/or its salts, and esters, particularly $C_4$ to $C_{18}$ esters of ascorbic acid, are added to the lipoic acid in compositions according to the present invention. Ascorbic acid, its salts, and esters, are collectively referred to herein as "ascorbic acid and/or ascorbic acid derivatives." Any number of hydroxyl groups on ascorbic acid may be acylated to obtain ascorbyl esters useful as additional ingredients in the practice of the invention. The more oxidation-resistant saturated fatty acid esters of ascorbic acid are preferred, including, but not limited to, ascorbyl laurate, ascorbyl myristate, ascorbyl palmitate, ascorbyl stearate, and ascorbyl behenate. Ascorbyl palmitate is used in one embodiment. As denoted herein, where fatty acid esters are described, e.g., ascorbyl stearate, compositions having predominantly that ester, e.g., predominantly stearate, are included. The esters may be prepared using hydrogenated oils or fats, or fractions thereof, and contain small amounts of another ester. Ascorbyl stearate prepared using canola, for example, commonly contain about 4% ascorbyl palmitate. Typical useful concentrations of ascorbic acid or ascorbic acid derivatives such as ascorbyl esters and/or their salts range from about 0.1% to about 5.0% by weight; some embodiments contain from about 0.25%-0.5%, in others 1% by weight. Lipoic acid has incorporated into stabilized ascorbyl compositions such as those set out in U.S. Pat. No. 6,162,419, which is hereby incorporated by reference.

Many preferred embodiments of this invention contain at least one or two, and sometimes several, other active ingredients in addition to lipoic acid and ascorbic acid and/or ascorbic acid derivatives, provided that the other active ingredient is not serine or N-acetyl serine. Preferred compositions contain essentially no serine and/or N-acetyl serine.

Tocotrienol may also be added to the composition of lipoic acid and ascorbic acid and/or ascorbic acid derivatives, particulary in embodiments containing an ascorbyl fatty acid. The term "tocotrienol" encompasses counterparts of tocopherol (vitamin E) that bear unsaturated tails, and include, but not limited to, α-, β-, γ-, and δ-tocotrienols, desmethyl-tocotrienol, didesmethyl-tocotrienol (occurring in sunflower seeds, vegetable oils, barley, brewer's grains, oats, and African violets), their synthetic counterparts, their counterparts having methylated or demethylated chroman rings, and mixtures thereof. The double bonds may be cis or trans or mixtures thereof.

In many embodiments utilizing tocotrienol in the composition, the tocotrienol is isolated from natural sources and added to the formulation as a tocotrienol-enriched vitamin E preparation. However, synthetic preparations may also be employed as well as mixtures of natural and synthetic vitamin E. Tocotrienol-enriched vitamin E preparations may be obtained by fractionating vitamin E preparations to remove a portion of tocopherols and recover a preparation more highly concentrated in tocotrienol. Useful tocotrienols are natural products isolated, for example, from wheat germ oil, bran, or palm oil using high performance liquid chromatography, or isolated by alcohol extraction and/or molecular distillation from barley, brewer's grain or oats. As used herein, the term "tocotrienols" includes tocotrienol-rich-fractions obtained from these natural products as well as the pure compounds. Tocotrienols containing essentially no tocopherol are used in some embodiments.

As with other vitamin E preparations, tocotrienol or tocotrienol-enriched preparations include those containing tocotrienol and, in some cases, tocopherol derivatives, particularly stabilized derivatives. These typically include derivatives related to the phenolic hydroxyl functionality, i.e., wherein it is acylated with an organic acid to form an ester. Examples of such stabilized tocotrienols include, but are not limited to, tocotrienol acetate, tocotrienol succinate, and mixtures thereof. However, the derivatives may also include those involving other reactive groups known to those skilled in the art. Where tocotrienol derivatives are employed, they must be functionally equivalent to tocotrienol. Preferred derivatives contain both the chromanol nucleus and three double bonds in the hydrocarbon tail.

Some embodiments optionally include at least one α-hydroxy acid ingredient to further augment the efficacy of compositions. α-Hydroxy acids include, but are not limited to, glycolic acid, hydroxymethylglycolic acid, lactic acid, glucuronic acid, galacturonic acid, gluconic acid, glucoheptonic acid, α-hydroxybutyric acid, α-hydroxyisobutyric acid, α-hydroxyvaleric acid, α-hydroxyisovaleric acid, α-hydroxycaproic acid, α-isocaproic acid, tartronic acid, tartaric acid, malic acid, hydroxyglutaric acid, hydroxyadipic acid, hydroxypimelic acid, muric acid, citric acid, isocitric acid, saccharic acid, dihydroxymaleic acid, dihydroxytartaric acid, and dihydroxyfumaric acid or derivatives of hydroxy acids such as pyruvic acid, methylpyruvate, ethyl pyruvate, isopropyl pyruvate, benzoylformic acid, methyl benzoylformate, and ethyl benzoylformate. Glycolic acid or lactic acid is particularly preferred.

The combination of tocotrienol or tocotrienol-enriched vitamin E preparations and/or a fat-soluble vitamin C fatty acid ester and/or a α-hydroxy acid, in a dermatologically acceptable carrier with lipoic acid and ascorbic acid and/or ascorbic acid derivatives is especially advantageous in compositions because lipoic acid augments the efficacy of the other ingredients in the formulation. The combination of two or more active ingredients readily solubilizes in the lipid-rich layers of the skin and together scavenge free radicals generated by ultraviolet radiation.

The effectiveness of the combination of lipoic acid and ascorbic acid and/or ascorbic acid derivatives with tocotrienols and/or α-hydroxy acids are unexpectedly effective compared to their use alone, or even compared to use of lipoic acid and ascorbic acid and/or ascorbic acid derivatives alone. The mechanism of the effect is not well understood, but may be related to the anti-oxidant properties of the active compounds and/or their interference with chemical reactions.

In terms of a possible explanation for the effectiveness of the active ingredients in the prevention or treatment of damage to the skin, it is noted that both lipoic acid and ascorbic acid, as antioxidants, can scavenge free radicals such as the oxygen radicals created by exposure of skin cells to ultraviolet radiation. Ascorbic acid is a powerful reducing agent that can prevent oxidative damage and regenerate chromanoxyl radicals formed as vitamin E derivatives scavenge radicals, reforming vitamin E that can scavenge more radicals. Preferred embodiments of this invention harness this synergestic effect.

The method of the present invention is particularly useful for the prevention and treatment of sunburn and other skin damage resulting from exposure to ultraviolet radiation. Compositions of lipoic acid and ascorbic acid and/or ascorbic acid derivatives, alone or with other active ingredients, can thus be added to dermatological creams and emollients as well as to commercial sunscreens to enhance their sun protection activity, or to burn creams used to treat sunburn.

Preparing a composition containing lipoic acid and ascorbic acid and/or ascorbic acid derivatives in a dermatologically acceptable carrier, as described herein, and applying such to exposed skin tissue prevents erythema and other damage to the skin induced by exposure to ultraviolet or solar radiation.

Further, compositions prepared as described herein prevent sunburn and skin damage and treating sunburn or sunburn skin damage.

In one hypothetical example, a composition may be prepared according to the present invention using a lecithin-based oil-in-water cream with lipoic acid at 1.0% by weight, and ascorbic acid also at 1.0% by weight, with ascorbyl palmitate at 0.5% by weight, tocotrienol acetate at 0.5% by weight and glycolic acid at 0.25% by weight. The lipoic/ascorbic acid cream would be applied to the skin of face of prior to solar exposure, and otherwise daily, for a period of two weeks to prevent skin damage and decrease erythema.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all modifications and variations be included within the scope of the invention. The claims are meant to cover the claimed components and steps in any sequence which is effective to meet the objectives there intended, unless the context specifically indicates the contrary.

What is claimed is:

1. A method for the reduction of erythema induced by exposure to ultraviolet or solar radiation, comprising: applying a composition containing lipoic acid, an α-hydroxy acids and ascorbic acid and/or ascorbic acid salts or esters or $C_4$ to $C_{18}$ esters in a dermatologically acceptable carrier to exposed skin tissue.

2. A method for the reduction of skin damage induced by exposure to ultraviolet or solar radiation, comprising: applying a composition containing lipoic acid, an α-hydroxy acids and ascorbic acid and/or ascorbic acid salts or esters or $C_4$ to $c_{18}$ esters in a dermatologically acceptable carrier to exposed skin tissue.

3. A method in accordance with claims 1 or 2, wherein said lipoic acid is about 0.1% to about 5.0% by weight of said composition.

4. A method in accordance with claim 3, wherein said lipoic acid is about 0.25% to about 3.0% by weight of said composition.

5. A method in accordance with claim 4, wherein said lipoic acid is about 0.5% to about 1.5% by weight of said composition.

6. A method in accordance with claims 1 or 2, wherein an amount of said ascorbic acid and/or ascorbic acid salts or esters or $C_4$ to $C_{18}$ esters is about 0.1% to about 5.0% by weight.

7. A method in accordance with claim 6, wherein an amount of said ascorbic acid and/or ascorbic acid salts or esters or $C_4$ to $c_{18}$ esters is about 0.5%-1.5% by weight of said composition.

8. A method in accordance with claim 1 or 2, wherein said ascorbic acid derivatives comprise fat-soluble fatty acid esters of ascorbic acid.

9. A method in accordance with claim 8, wherein said fat-soluble fatty acid esters of ascorbic acid consist of ascorbyl palmitate.

10. A method in accordance with claims 1 or 2, wherein said composition further comprises one or more additional ingredients selected from the group consisting of: tocotrienols and vitamin E compositions enriched with tocotrienols.

11. A method in accordance with claim 1, wherein said α-hydroxy acid comprises glycolic acid or lactic acid.

12. A method in accordance with claim 1 wherein an amount of said α-hydroxy acid is about 0.1% to about 5.0% by weight of said composition.

13. A method in accordance with claim 10 wherein an amount of said tocotrienols and vitamin E compositions enriched with tocotrienols is about 0.1% to about 5.0% by weight of said composition.

14. A method in accordance with claim 10 wherein said lipoic acid is about 0.1% to about 5.0% by weight of said composition.

15. A method in accordance with claim 13, wherein said lipoic acid is about 0.25% to about 3.0% by weight of said composition.

\* \* \* \* \*